(12) United States Patent
Duong et al.

(10) Patent No.: US 7,909,227 B2
(45) Date of Patent: Mar. 22, 2011

(54) CRYOSURGICAL PROBE WITH VACUUM INSULATION TUBE ASSEMBLY

(75) Inventors: Thach Duong, Tustin, CA (US); Jenny C. Liu, Irvine, CA (US); Jay J. Eum, Irvine, CA (US)

(73) Assignee: Endocare, Inc., Austin, TX (US)

( * ) Notice: Subject to any disclaimer, the term of this patent is extended or adjusted under 35 U.S.C. 154(b) by 1070 days.

(21) Appl. No.: 11/613,054

(22) Filed: Dec. 19, 2006

(65) Prior Publication Data

US 2008/0147055 A1    Jun. 19, 2008

(51) Int. Cl.
*B23K 37/04* (2006.01)
(52) U.S. Cl. .................................. 228/44.5; 228/49.3
(58) Field of Classification Search .................. None
See application file for complete search history.

(56) References Cited

U.S. PATENT DOCUMENTS

| | | | |
|---|---|---|---|
| 5,573,532 A * | 11/1996 | Chang et al. | 606/26 |
| 6,475,212 B2 | 11/2002 | Dobak | |
| 6,478,213 B1 * | 11/2002 | Higgins | 228/133 |
| 6,767,346 B2 | 7/2004 | Damasco | |
| 6,769,163 B2 * | 8/2004 | Van Cleve | 29/447 |
| 6,786,902 B1 | 9/2004 | Rabin | |
| 7,374,063 B2 | 5/2008 | Reid | |
| 2003/0055415 A1 | 3/2003 | Yu | |
| 2004/0004478 A1 * | 1/2004 | Hofmann et al. | 324/321 |
| 2004/0024391 A1 | 2/2004 | Cytron | |
| 2005/0122107 A1 * | 6/2005 | Hasegawa et al. | 324/318 |
| 2005/0192565 A1 | 9/2005 | Eum | |
| 2007/0007963 A1 * | 1/2007 | Kawasaki et al. | 324/321 |
| 2007/0257673 A1 * | 11/2007 | Nakahara et al. | 324/315 |

* cited by examiner

*Primary Examiner* — Kiley Stoner
(74) *Attorney, Agent, or Firm* — Lawrence N. Ginsberg (57) ABSTRACT

A vacuum insulation tube assembly which is utilized as a component in a cryosurgical probe. The vacuum insulation tube assembly includes an inner tube; and, an outer tube concentrically positioned about the inner tube. The outer tube is securely soldered at end portions of the inner tube and forms a vacuum space between the inner tube and the outer tube. The vacuum tube assemblies may be conveniently mass produced using a special fixture.

5 Claims, 6 Drawing Sheets

CRYOSURGICAL PROBE WITH VACUUM INSULATION TUBE ASSEMBLY

BACKGROUND OF THE INVENTION

1. Field of the Invention

The present invention relates to cryosurgical probes and more particularly to a cryosurgical probe with an improved vacuum insulation tube assembly and method of manufacture thereof which facilitates economical mass production of precision cryosurgical probes.

2. Description of the Related Art

Cryosurgery involving the use of a cryosurgical probe assemblies typically involves the use of cryoprobes that are each attached to a handle that are, in turn, connected to a high-pressure fluid line with a quick-disconnect for attachment to a fluid source.

Cryosurgical probes manufactured by present assignee Endocare, Inc., Irvine, Calif., utilize a vacuum insulation tube that provides selected non-cooling areas on the surface of the cryoprobe. For example, U.S. Pat. Publication US 20050192565 (U.S. patent Ser. No. 11/116,873), to Eum et al, entitled "Detachable Cryosurgical Probe With Breakaway Handle", incorporated in its entirety herein by reference, discloses such a cryosurgical probe with a vacuum tube. The vacuum tube comprises an inner tube positioned within an outer tube. A vacuum is formed between the two tubes and the ends of the tubes are joined by brazing.

Another example of a cryosurgical probe that uses a vacuum tube is disclosed in U.S. Pat. No. 5,573,532, issued to Z. H. Chang, entitled "Cryogenic Surgical Instrument and Method of Manufacturing the Same". Again, in this instance the vacuum is formed by brazing.

In all known cryosurgical probes that use these vacuums for insulation the tubes are formed by brazing. Brazing is a relatively expensive endeavor.

SUMMARY OF THE INVENTION

In a broad aspect, the present invention is embodied as a vacuum insulation tube assembly which is utilized as a component in a cryosurgical probe. The vacuum insulation tube assembly includes an inner tube; and, an outer tube concentrically positioned about the inner tube. The outer tube is securely soldered at end portions of the inner tube and forms a vacuum space between the inner tube and the outer tube.

The vacuum tube assemblies may be mass produced using a special fixture. The fixture includes a generally cylindrical vacuum chamber having an upper end, a lower end, and a central axis. A bottom plate is positioned within an interior volume of the vacuum chamber, at the lower end. The bottom plate includes a plurality of spaced elongated bottom plate openings extending therethrough substantially parallel to the central axis. A guide plate assembly is securely supported within the interior volume, at the upper end. The guide plate comprises a plurality of spaced elongated guide plate openings extending therethrough substantially parallel to the central axis. A support plate is securely positioned within an intermediate portion of the interior volume. The support plate includes a plurality of spaced elongated support plate openings extending therethrough substantially parallel to the central axis. A cover assembly is mounted on the upper end of the vacuum chamber for providing access to the vacuum chamber for a plurality of inner tubes and outer tubes that are used to form vacuum insulation tube assemblies. The bottom plate openings, the guide plate openings, and the support plate openings provide access for insertion of the outer tubes and the inner tubes. The lower end of said vacuum chamber has a vacuum conduit in fluid communication with lower ends of the vacuum tube assembly, for connection to a vacuum source for evacuating fluid in spaces between the outer tubes and the inner tubes when concentrically positioned, ends of each respective tube assembly being soldered during operation of the fixture to form the vacuum tube assemblies.

DETAILED DESCRIPTION OF THE INVENTION

Figure 1:
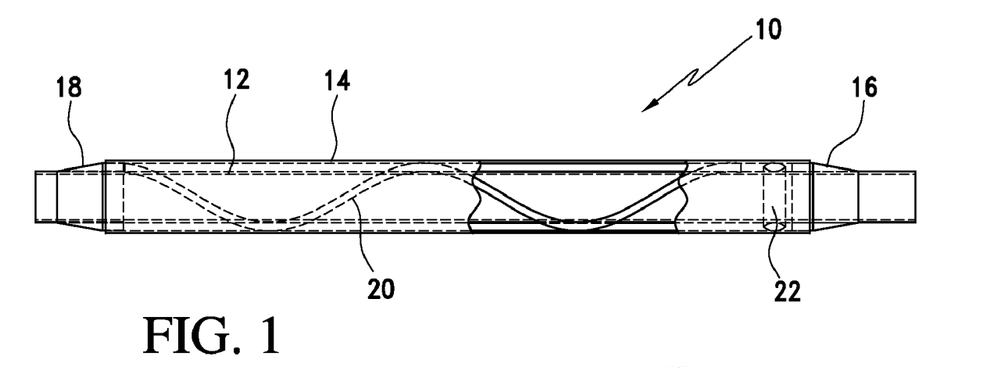
FIG. 1 is a cross-sectional view of the vacuum insulation tube assembly of the present invention.

Referring now to the drawings and the characters of reference marked thereon, FIG. 1 illustrates a preferred embodiment of the vacuum insulation tube assembly of the present invention, designated generally as 10. The vacuum insulation tube assembly 10 is utilized as a component in a cryosurgical probe, as will be described below in more detail. It includes an inner tube 12; and, an outer tube 14 concentrically positioned about the inner tube 12. The outer tube 14 is securely soldered at end portions 16, 18 of the inner tube 12 to form a vacuum space between the inner tube 12 and the outer tube 14. The tubes are preferably formed of stainless steel or titanium alloy. The vacuum insulation tube assembly 10 includes a thermally insulative spacing element 20 positioned between the inner tube 12 and the outer tube 14. The spacing element is helically twisted about the inner tube 12. It is preferably formed of a ceramic material such as ceramic fiber. The vacuum insulation tube assembly 10 also includes an o-ring 22 that is leftover during the manufacturing process for the assembly 10, as will be discussed below.

Figure 2:
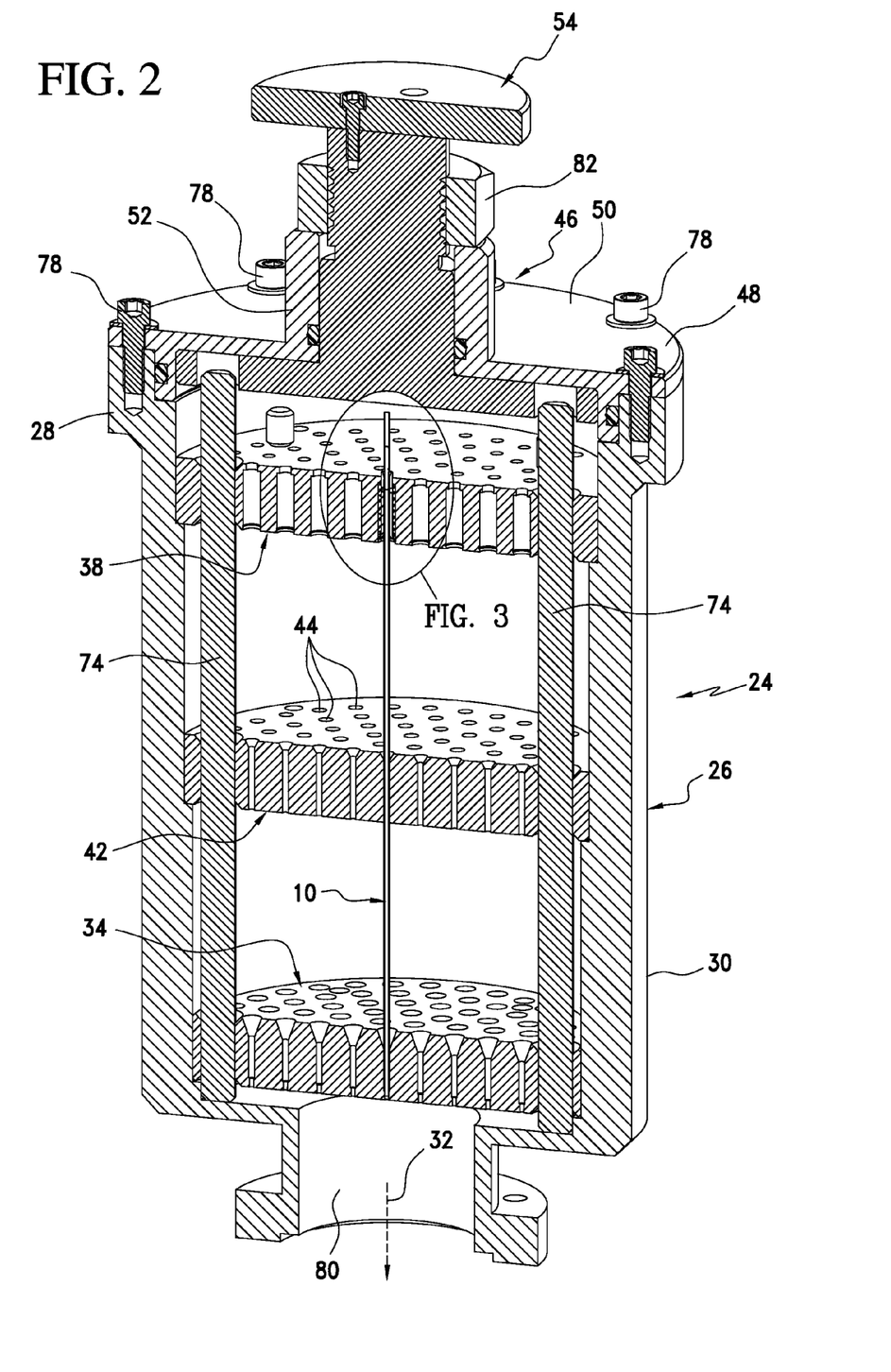
FIG. 2 is a cutaway perspective illustration of the fixture used to mass produce the vacuum insulation tube assemblies of FIG. 1.

Referring now to FIG. 2, the fixture for manufacturing vacuum insulation tube assemblies 10 in mass quantities is illustrated, designated generally as 24. The fixture 24 includes a generally cylindrical vacuum chamber 26 having an upper end 28, a lower end 30, and a central axis 32. A bottom plate 34 is positioned within an interior volume of the vacuum chamber 26, at the lower end 30. The bottom plate 34 includes a plurality of spaced elongated bottom plate openings 36 extending therethrough substantially parallel to the central axis 32. A guide plate assembly 38 is securely supported within the interior volume, at the upper end 28. The guide plate comprises a plurality of spaced elongated guide plate openings 40 extending therethrough substantially parallel to the central axis 32. A support plate 42 is securely positioned within an intermediate portion of the interior volume. The support plate includes a plurality of spaced elongated support plate openings 44 extending therethrough substantially parallel to the central axis 32.

A cover assembly 46 is mounted on the upper end 28 of the vacuum chamber 26 for providing access to the vacuum chamber 26 for a plurality of inner tubes 12 and outer tubes 14 that are used to form vacuum insulation tube assemblies 10. The cover assembly 46 includes a cover element 48 including a circular main portion 50 and a central portion having a circular flange 52. It also includes an ejector plate assembly 54 securely positionable on the end of the circular flange 52.

Figure 3:
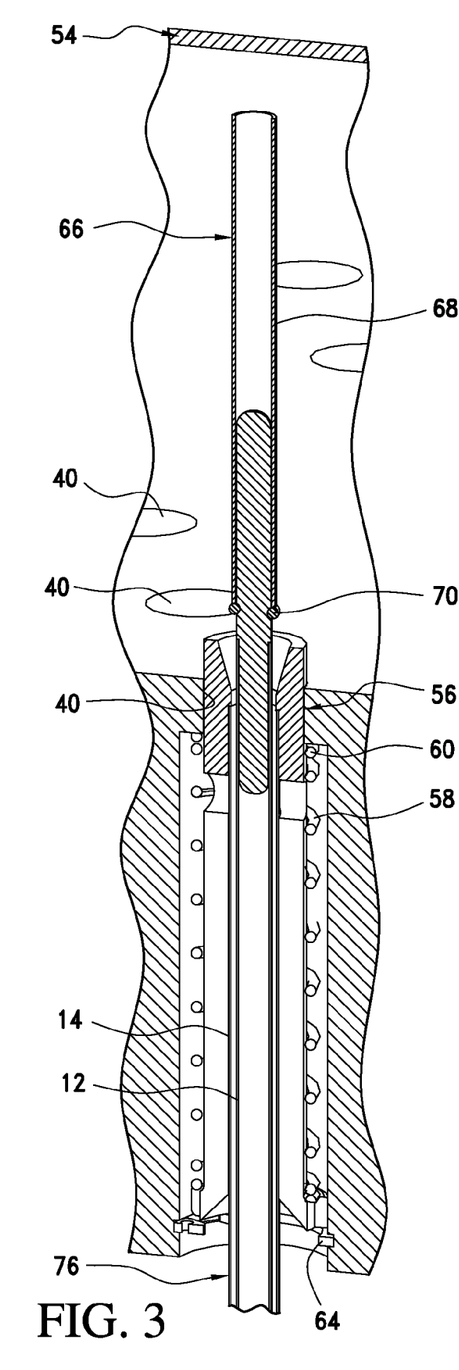
FIG. 3 is an enlarged cutaway perspective view taken along line 3-3 of FIG. 2.

Referring now to FIG. 3, an enlarged view of the guide plate assembly 38, it can be the guide plate assembly 38 includes a plurality of tapered slider assemblies, each designated generally as 56. Each tapered slider assembly 56 includes a spring 58 positioned within a recessed portion 60 of an associated guide plate assembly opening 40. An elongated tapered slider element 62 is positioned within the spring 58—an upper portion of an internal surface of the tapered slider element 62 being tapered. A retainer ring 64 is positioned within the guide plate assembly opening 40 for retaining the elongated tapered slider element 62.

Figure 4:
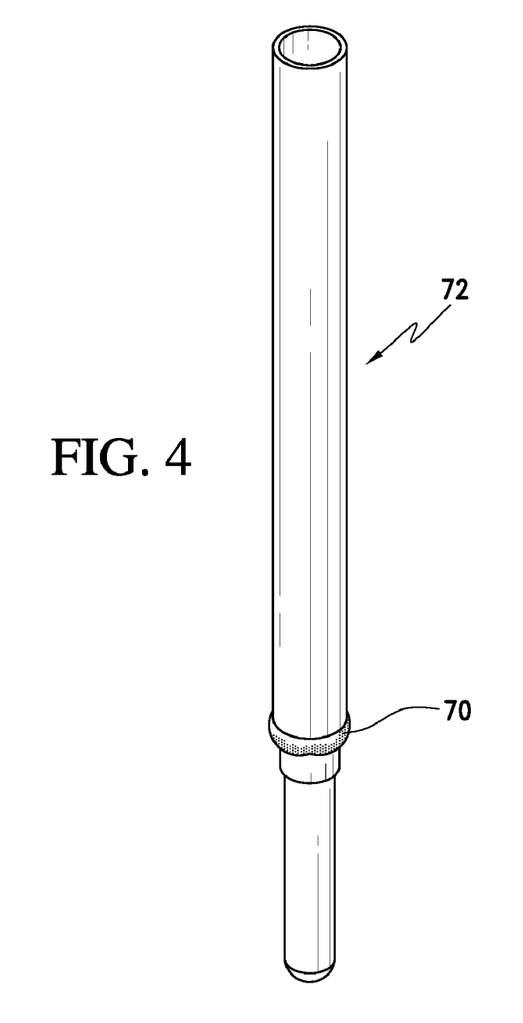
FIG. 4 is an enlarged perspective view of the o-ring insert pin shown in FIG. 3.

Each tapered slider assembly 62 cooperates with an associated o-ring plunger assembly, designated generally as 66. Each o-ring plunger assembly 66 includes an o-ring plunger element 68 operatively positionable within the internal surface of the elongated tapered slider element 62 for urging an o-ring 70 into a desired position between the outer tube 14 and the inner tube 12. An o-ring insert pin 72 is operatively positionable within the o-ring plunger 68 for supporting the o-ring 70. An enlarged view of an o-ring insert pin 72 is shown in FIG. 4.

In the manufacture of multiple vacuum insulation tube assemblies 10, the bottom plate is first securely positioned at the lower end of the vacuum chamber 26. Two guide pins 74 are then inserted which prevent undesired rotation of the various parts of the fixture 24. The support plate is then slid into position, as shown in FIG. 2.

Next, precursor inner/outer tube assemblies 76 are fitted through the support plate openings 44 and into the bottom plate openings 36. Each precursor inner/outer tube assembly 76 comprises an outer tube 14 concentrically positioned about an inner tube 12. The fixture 24 may contain about a hundred precursor inner/outer tube assemblies 76. Each precursor inner/outer tube assembly 76 is soldered at one (i.e. bottom) end thereof.

The guide plate assembly 38 is then securely positioned within the interior volume, at the upper end 28. The guide plate assembly 38 is positioned to provide access to the precursor inner/outer tube assemblies 76 through the spaced elongated guide plate openings 40. The guide plate assembly 38 has been pre-fitted with tapered slider assemblies 56. O-ring plunger assemblies 66 are then installed into desired positions relative to associated spaced elongated guide plate openings 40 and their associated tapered slider assemblies 56.

Figure 5:
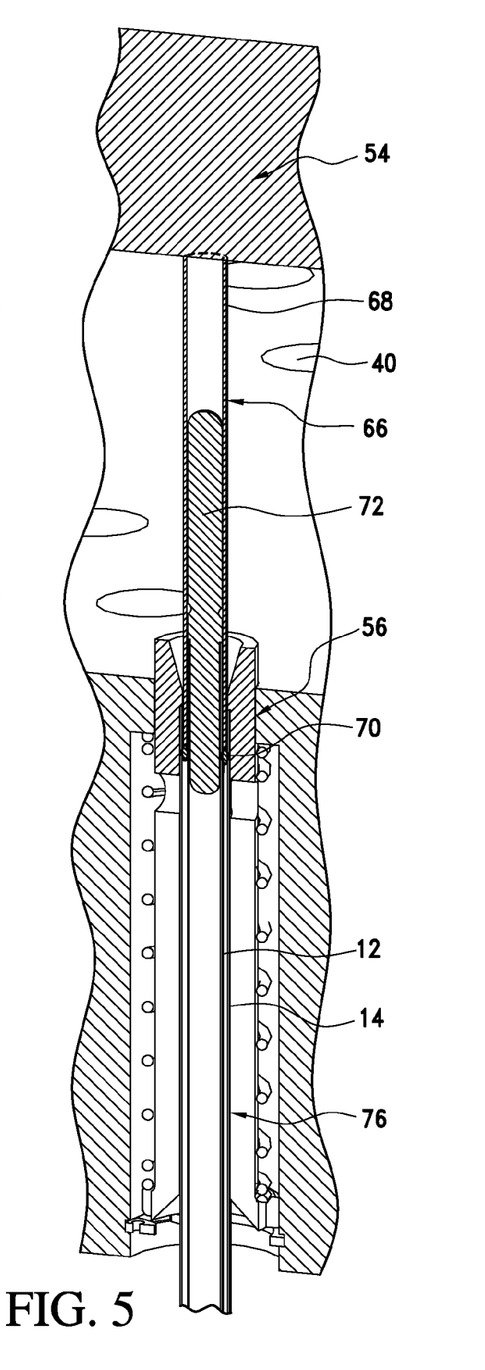
FIG. 5 is an enlarged perspective view taken in the same region as that illustrated in FIG. 3.

The cover assembly 46 is then mounted on the upper end of the vacuum chamber 26 via cover screws 78. A vacuum is then applied via connection of a vacuum conduit 80 to a vacuum pump (not shown). After the vacuum chamber 26 is evacuated, a nut 82 of the cover assembly 46 is loosened, allowing the ejector plate assembly 54 to slide down (by the pressure difference), concomitantly applying a force on the o-ring plunger 68. This is shown in FIG. 5. The o-ring plunger 68 pushes the o-ring insert pin 72 containing the o-ring 70 into the desired position between the outer tube 12 and the inner tube 14. The o-ring 70 serves as a temporary seal.

The cover assembly 46 is then removed to allow removal of the precursor inner/outer tube assemblies 76. The previously unsoldered ends of the precursor inner/outer tube assemblies 76 are then soldered to form completed vacuum insulation tube assemblies 10. Prior to soldering, the outer tube 12 is preferably crimped against the inner tube 14 to expel residual air.

The present technique obviates the large investment required for vacuum brazing techniques. However, it offers the advantage of allowing high volume efficiency using these soldering techniques.

Figure 6:
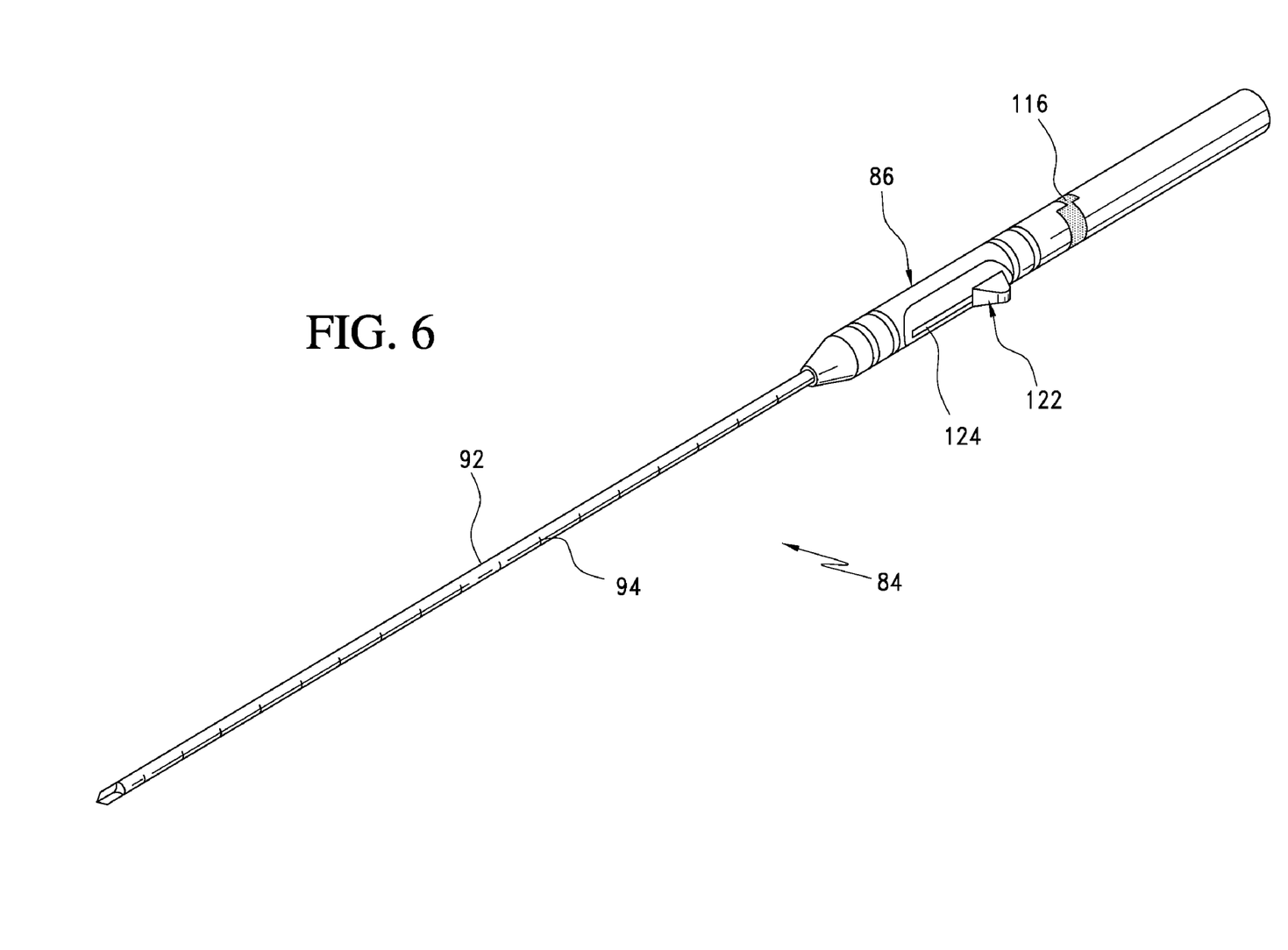
FIG. 6 is a perspective view of a disposable probe assembly of a cryosurgical probe that utilizes the vacuum insulation tube assembly of the present invention.

Referring now to FIG. 6, utilization of the completed vacuum insulation tube assembly 10 within a cryosurgical probe is illustrated, the cryosurgical probe being designated generally as 84. The cryosurgical probe shown in this example application is of a disposable type. Additionally, it is adjustable so as to allow for variations in the size of the generated ice ball. This type of cryosurgical probe is shown for the purposes of illustration and not limitation. Other types of cryosurgical probes can use the vacuum insulation tube assemblies produced in accordance with the principles of the present invention.

Figure 7:
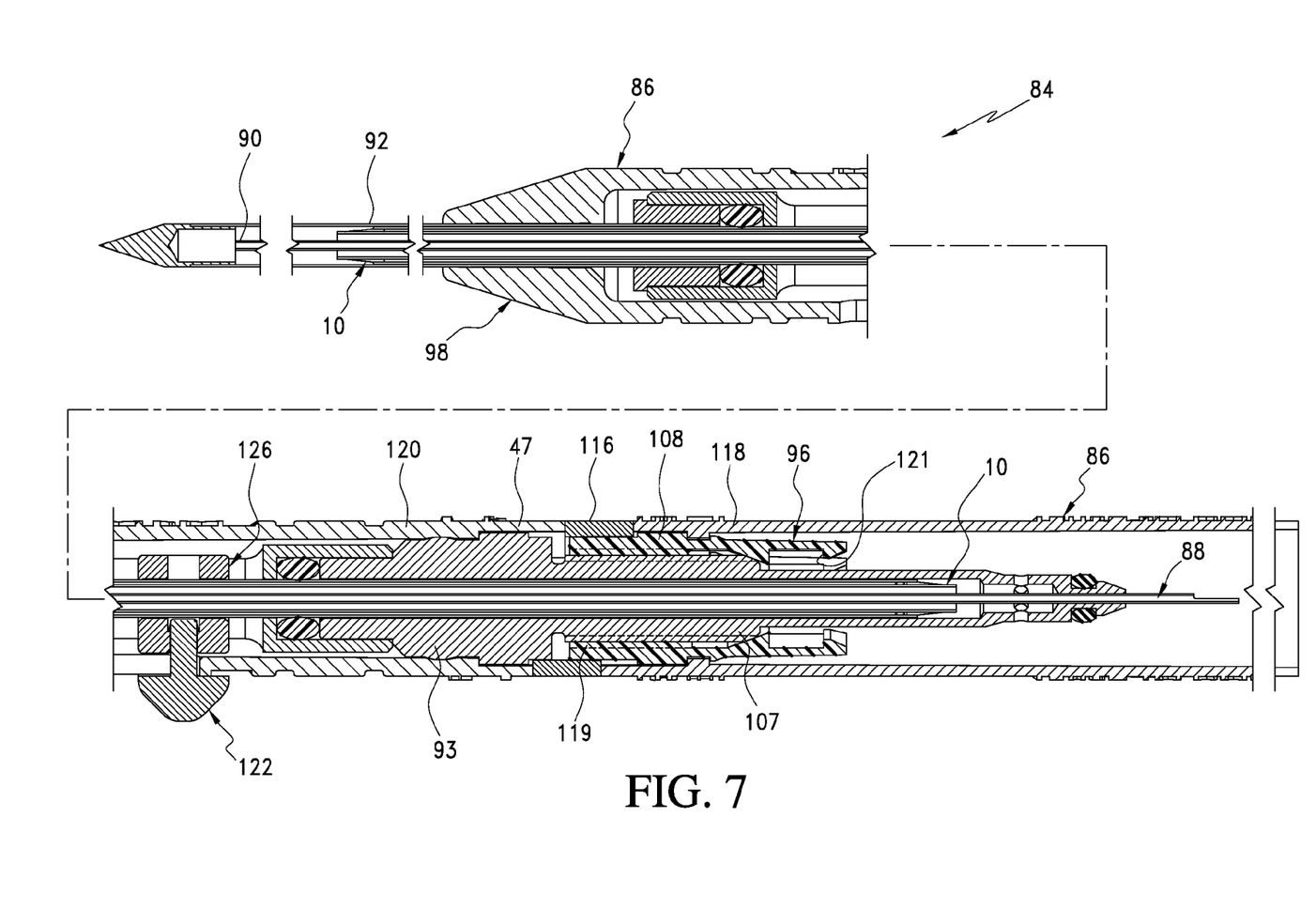
FIG. 7 is a cross-sectional view of the disposable probe assembly, the view being broken away in a few sections to emphasize the various portions of the disposable probe assembly.

As can be seen in FIG. 7, the cryosurgical probe 84 includes a disposable probe assembly, designated generally as 86 and a reusable probe assembly (discussed in more detail below). FIG. 7 is broken away in a few places for the purposes of clarity. The reusable probe assembly includes a Joule-Thomson tube 88 that is connected at an inlet section to a source (not shown) of cryogenic fluid. The fluid source may be, for example, a cryosurgical system such as that manufactured by present assignee, Endocare, Inc., Irvine, Calif., trademarked under the name of CRYOCARE CS™. Such a cryosurgical system typically utilizes argon gas from an argon gas source to provide Joule-Thomson cooling of the cryosurgical probes. Alternatively, nitrogen can be used. Alternatively, a fluid supply system can be utilized that does not require an external fluid supply source. Heating of the cryosurgical probes is typically provided by a helium gas source for providing a helium gas flow through the Joule-Thomson nozzle 90 of the cryosurgical probe. This provides a heating effect. Such heating of the cryosurgical probes is provided to unstick the probes from the treated tissue for cryoprobe removal. A gas delivery assembly of the disposable probe assembly 86 includes a fluid conduit subassembly that includes a shaft 92 and the Joule-Thomson tube 88. A stem 93 is bonded to the shaft 92. The shaft 92 has a freezing zone. The fluid conduit subassembly is for delivering and returning cooling fluid used for cryogenic cooling. Spaced markings 94 may be provided on the outer surface of the cryosurgical probe 84. These markings 94 may be, for example, at 1 cm intervals.

The disposable probe assembly 86 of the cryosurgical probe 84 includes a finger lock assembly including finger lock element 96, and a disposable handle assembly 98. The finger lock assembly provides detachment of the disposable probe assembly 86 as discussed in detail in U.S. Pat. Publication No. US 20050192565 (U.S. patent Ser. No. 11/116, 873) entitled, "Detachable Cryosurgical Probe With Breakaway Handle", assigned to the present assignee, which has been discussed above, has been incorporated herein by reference in its entirety.

Figure 8:
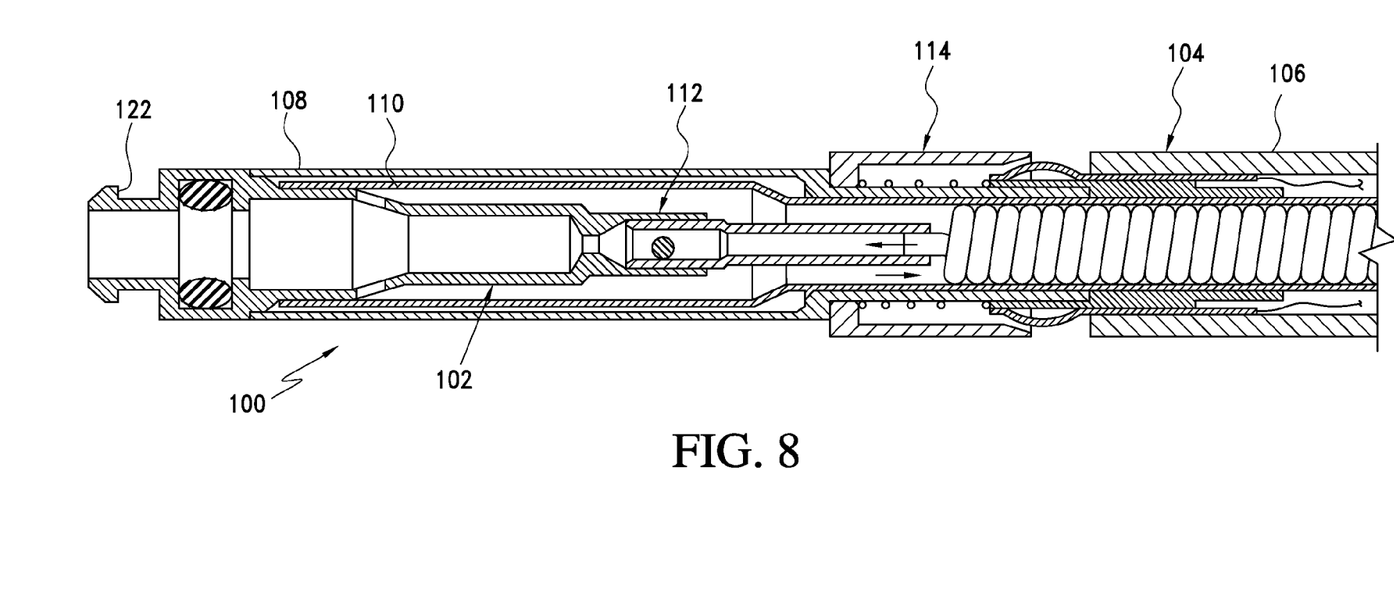
FIG. 8 is a cross-sectional view of a reusable probe assembly of the cryosurgical probe.

Referring now to FIG. 8, the reusable probe assembly 100 includes the manifold assembly 102 and a reusable handle assembly 104 secured about the periphery of the manifold assembly 102. The reusable handle assembly 104 includes a first end portion 106 and a second end portion 108. The manifold assembly 102 includes an outer covering 110.

The reusable probe assembly 100 preferably includes a safety valve assembly, designated generally as 112, operatively engaged with the manifold assembly 102 for impeding cryogenic working fluid flow when the disposable probe assembly 86 is detached from the reusable probe assembly 100.

The reusable probe assembly also preferably includes an electrical confirmation assembly, designated generally as 114, operatively engaged with the disposable probe assembly 86 for providing electrical confirmation that the disposable probe assembly 86 is connected.

During use, when the disposable probe assembly 86 is attached, a breakaway collar 116 is an integral unit that prevents relative rotation between the proximal handle section 118 and the distal handle section 120. In this configuration, the lip 121 engages an associated lip 122 of the manifold assembly 102 of the reusable probe assembly 100; thereby securing the reusable probe assembly 100 to the disposable probe assembly 86. During an initial stage of detachment of the disposable probe assembly 86, the user rotates the distal handle section in a first direction relative to the proximal handle section 118 to "break away" breakaway surfaces of the breakaway collar 116, allowing the breakaway collar 116 to radially expand. During an intermediate stage of detachment of the disposable probe assembly 86 the user counter rotates the distal handle section 120 in an opposite second direction relative to the proximal handle section 118. The relative rotation between the distal handle section 120 and the proximal handle section 118 provides axial movement of the distal handle section 120 toward the proximal handle section 118 via the engagement of the threaded inner surface 119 of the distal finger lock element section and the threaded outer surface of the stem 107. The axial movement is enabled by the radial expansion of the breakaway collar 116. The ramped surfaces of the radially spaced fingers 96 engage the associated ramp section on the stem 107 during the axial movement thereby urging the fingers 96 to open. During a final stage of detachment, the fingers 96 open sufficiently to allow disengagement of the lip 121 from the associated lip 122 of the reusable probe assembly, thus enabling the disposable probe assembly 86 to be detached from the reusable probe assembly 100.

The vacuum insulation tube assembly 10 may be repositioned as desired relative to the shaft 92. This is accomplished by actuating a button assembly, designated generally as 122, along a guideway 124. This is discussed in detail in U.S. Pat. Publication No. US 20050192565 (U.S. patent Ser. No. 11/116,873) mentioned above. Briefly, a slider assembly 126 is mechanically connected to the vacuum tube 10 and to the button assembly 122. Thus, the shaft 92 and the vacuum tube 10 are capable of moving relative to each other. The button assembly 122 can be locked into position to prevent unintentional movement. Thus, the size and shape of the generated iceball can be varied in accordance with a specific desired need.

During operation, with the disposable probe assembly 86 attached to a reusable probe assembly, cryogenic fluid originating from (typically) an argon tank flows through the supply line through the manifold assembly of the reusable probe assembly. The flow is directed through the central passageway in the high pressure stem 107 via J-T tube 88, and out of the J-T port 90.

After being expelled from the J-T port 90 the return fluid is directed in the space between the inner surface of the inner tube 12 of the vacuum insulation tube assembly 10 and the outer surface of the J-T tube 88. It then flows through openings in the manifold assembly. The return fluid is eventually expelled via a hose of the cryosurgical probe assembly.

In the device illustrated the cryosurgical probe is shown with a pointed tip to provide insertion into the patient's tissue for the desired application. However, it is understood that the tip may be blunt, depending on the application. For example, for certain applications direct insertion is desirable. For other applications, insertion via a cannula/introducer is preferred.

Although application of this device utilizing CT guidance is preferred, the cryosurgical probe 10 may be used with a variety of guidance tools, such as MRI and ultrasound. In one preferred implementation ultrasound is used for initial guidance, followed up with CT for final confirmation.

Although the present invention has been discussed above with respect to a cryosurgical probe having a rigid outer sheath, the cryosurgical probe may be made to be malleable by including at least one malleable segment thereon. Malleable segments are formed of material that permit reshaping and bending to reposition the ablating surface for greater ablation precision. An example of a cryosurgical probe having malleable characteristics is disclosed and claimed in our co-pending patent application U.S. patent Ser. No. 09/957,337, U.S. Pat. Publication No. US 2003/0055415 A1, published on Mar. 20, 2003 entitled "Malleable Cryosurgical Probe", incorporated in its entirety herein by reference.

One method for providing malleable characteristics includes providing a malleable shaft with a bellows portion. U.S. Pat. No. 6,767,346, issued to Damasco, et al. entitled "Cryosurgical Probe With Bellows Shaft", incorporated in its entirety herein by reference, discloses use of a bellows portion for providing the necessary reshaping and bending.

The cryosurgical probe may be constructed to have various angles. For example, a right angled probe is particularly advantageous for interventional radiological applications.

If the detachable cryosurgical probe is utilized in combination with ultrasound the outer sheath may have an echogenic coating with, for example, a porous microstructure having the ability to trap microscopic air bubbles. This creates thousands of highly efficient ultrasound reflectors on the surface of the sheath.

Thus, while the preferred embodiments of the devices and methods have been described in reference to the environment in which they were developed, they are merely illustrative of the principles of the invention.

For example, even though the vacuum insulation tube assembly has been described specifically with respect to the present cryosurgical probe it is understood that it can be used on other types of cryosurgical probes that, for example, may not be single use.

Although the cryosurgical probe system is particularly advantageous for prostate cryosurgery it is also advantageous for many other types of ablation applications, such as radiological applications.

Other embodiments and configurations may be devised without departing from the spirit of the invention and the scope of the appended claims.

The invention claimed is:

1. A fixture for use in manufacturing a vacuum insulation tube assembly for a cryosurgical probe, comprising:
   a) a generally cylindrical vacuum chamber having an upper end, a lower end, and a central axis;
   b) a bottom plate positioned within an interior volume of said vacuum chamber, at said lower end, said bottom plate comprising a plurality of spaced elongated bottom plate openings extending therethrough substantially parallel to said central axis;

c) a guide plate assembly securely supported within said interior volume, at said upper end, said guide plate comprising a plurality of spaced elongated guide plate openings extending therethrough substantially parallel to said central axis;

d) a support plate securely positioned within an intermediate portion of said interior volume, said support plate comprising a plurality of spaced elongated support plate openings extending therethrough substantially parallel to said central axis; and, e) a cover assembly mountable on said upper end of said vacuum chamber for providing access to said vacuum chamber for a plurality of inner tubes and outer tubes that are used to form vacuum insulation tube assemblies;

wherein said bottom plate openings, said guide plate openings, and said support plate openings provide access for insertion of the outer tubes and the inner tubes, said lower end of said vacuum chamber having a vacuum conduit in fluid communication with lower ends of the vacuum tube assembly, for connection to a vacuum source for evacuating fluid in spaces between the outer tubes and the inner tubes when concentrically positioned, ends of each respective tube assembly being soldered during operation of said fixture to form the vacuum tube assemblies.

2. The fixture of claim 1, wherein said cover assembly, comprises:

a) a cover element including a circular main portion and a central portion having a circular flange; and, b) an ejector plate assembly securely positionable on the end of said circular flange.

3. The fixture of claim 1, further comprising a plurality of guide pins securely positionable within said vacuum chamber for supporting said bottom plate, said guide plate assembly and said support plate in their respective positions.

4. The fixture of claim 1, wherein said guide plate assembly further comprises a plurality of tapered slider assemblies, each comprising:

a) a spring positioned within a recessed portion of an associated guide plate assembly opening;

b) an elongated tapered slider element positioned within said spring, an upper portion of an internal surface of said tapered slider element being tapered; and, c) a retainer ring positioned within said guide plate assembly opening for retaining said elongated tapered slider element.

5. The fixture of claim 4, further comprising a plurality of o-ring plunger assemblies, each comprising:

a) an o-ring plunger element operatively positionable within said internal surface of said elongated tapered slider element for urging an o-ring into a desired position between said outer tube and said inner tube; and, b) an o-ring insert pin operatively positionable within said o-ring plunger for supporting said o-ring.

* * * * *